May 11, 1943. R. L. BYRUM Plant Pat. 582
ROSE PLANT
Filed Jan. 20, 1942
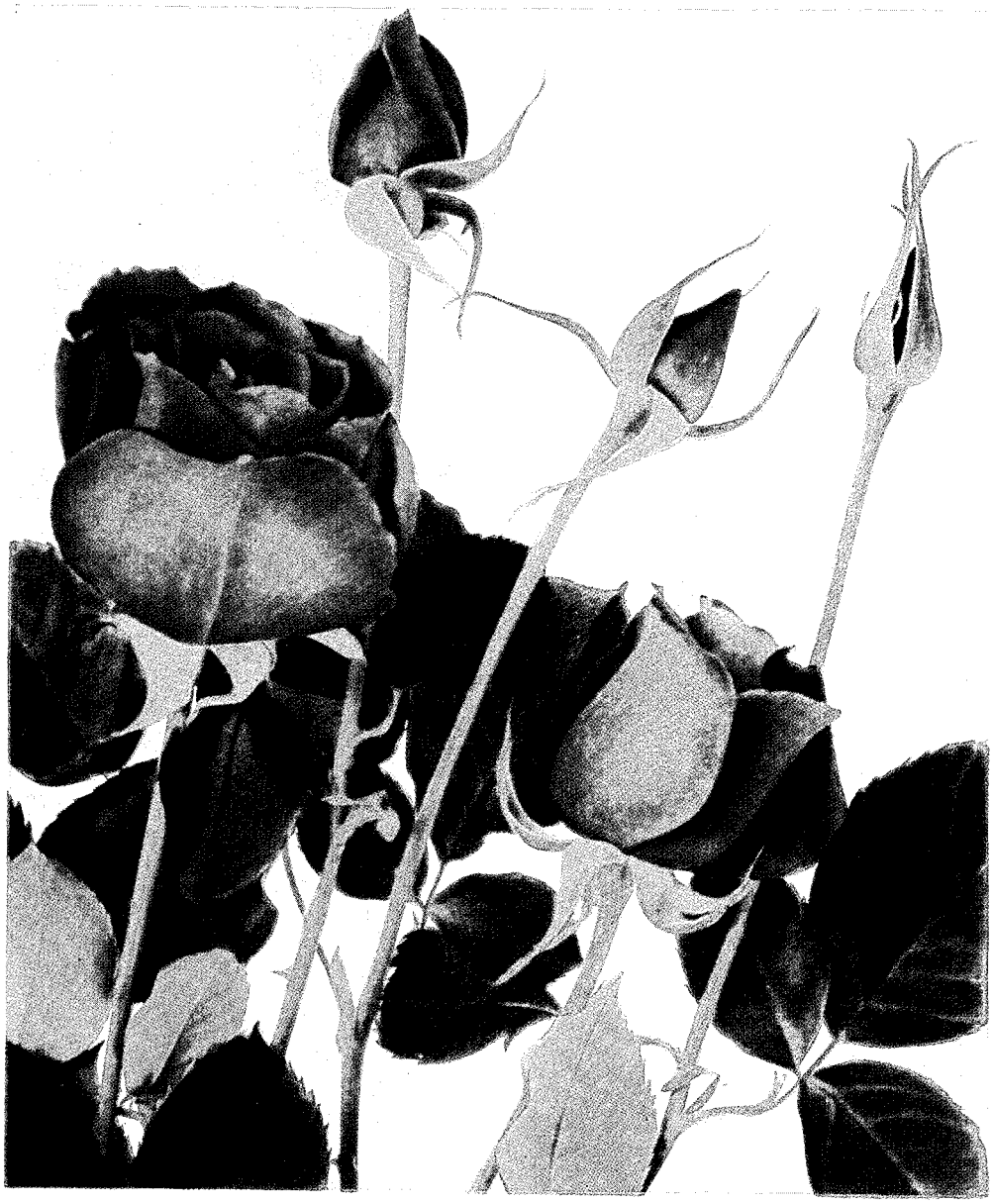
Inventor
Roy L. Byrum
By Robb & Robb
Attorneys Patented May 11, 1943 Plant Pat. 582

UNITED STATES PATENT OFFICE

582

ROSE PLANT

Roy L. Byrum, Richmond, Ind., assignor to Joseph H. Hill Company, Richmond, Ind., a corporation of Indiana Application January 20, 1942, Serial No. 427,507

1 Claim. (Cl. 47—61)

The present invention relates to a new and distinct variety of rose plant of the hybrid tea class, the result of a definite effort to produce a rose having as many of the desirable features of the parents but eliminating the undesirable characteristics.

It may be noted that the seed parent of the present variety is an unnamed seedling having a dark velvety red color and a small bloom which was in reality too large to be classed as a miniature and too small to be considered a satisfactory one of standard size. Its habit of growth was free and it was very fragrant.

In crossing the two parent varieties hereinafter noted, the object in mind was to obtain the color of the seed parent with the size of bloom of the pollen parent "Chieftain," Plant Patent No. 150. As a result of this cross a larger size bloom was obtained and at the same time it was found that the new variety also produced better foliage than the seed parent, but the cross apparently went to the garden rose type and greenhouse forcing type.

It is also to be noted, as hereinafter specified, that the blooms borne by the plants grown out-of-doors during the summer months are much darker than the blooms on the plants grown in the greenhouse. The coloring of these blooms appears to be different from any of the color tones shown in Ridgway's Color Chart, but they are very similar in color to the blooms of "Crimson Glory," Plant Patent No. 105. There is also a distinct difference in the habit of growth of the new rose, and the intermediate and inner petals of the open bloom have a brighter hue than do those of "Crimson Glory."

From the foregoing the present rose embodies distinct differences in characteristics from roses of the same class and other differences will be apparent from the following detailed description, the color terminology used therein referring to Ridgway's Color Chart as nearly as found applicable by way of comparison, the dictionary meaning being otherwise applicable.

Type: Half hardy; tall, bush; greenhouse and outdoor; for cut flowers and garden decoration.

Class: Hybrid tea.

Parentage:

*Seed parent.*—An unnamed seedling having as its parents an unnamed seedling and "Mills' Sport of Premier," both the seed and pollen parents being similar in color to the well known variety "Lucile Hill."

*Pollen parent.*—"Chieftain."

Propagation: The distinguishing characteristics have been found to come true to form by the following methods of reproduction which are the only ones tried: by cuttings, grafting and budding.

*Flower*

Locality where grown: Richmond, Indiana.

Flowers borne: Singly to stem; in irregular clusters; on normal, strong, medium length stems.

Quantity of bloom: Abundant, outdoors and in greenhouse.

Continuity: Continuous in greenhouses.

Fragrance: Strong; tea.

Bud:

*Peduncle.*—Short; medium heavy; erect, stiff; reddish, green; almost smooth; few red hairs.

*Before calyx breaks.*—*Size*—medium. *Form*—short, pointed, globular, with foliaceous appendages on the surface of the bud; with slender, much cut foliaceous parts extending beyond the tip of the bud equal to ¼ and in some instances ½ of its length.

*As calyx breaks.*—*Color*—Victoria Lake, Plate I.

*As first petal opens.*—*Size*—medium. *Form*—short, pointed, globular. *Color*: outside—Carmine, Plate I, overlaid with Ox-blood Red, Plate I; inside—Carmine, Plate I, overlaid with velvety covering. *Opening*—it does open up well.

Bloom:

*Size.*—Medium; 4 inches to 4½ inches.

*Petalage.*—Semi-double; from fifteen to twenty-five arranged irregularly.

*Form.*—Globular at first; becoming open; petals remaining at first loosely rolled outward; becoming later, at maturity, very loosely rolled outward.

Petals: Thick, with inside satiny, velvety; outside shiny, satiny.

*Shape.*—Outside—obovate, with 1 notch. Intermediate—obovate, with 1 notch. Inside—obovate, with 1 notch.

This description of a newly opened flower was made from a rose grown in a greenhouse, in the month of September, 1941, at Richmond, Indiana.

*Color.*—Outside petal: outside surface—Carmine, Plate I, blotched with Pomegranate Purple, Plate XII; inside surface—Carmine and Ox-blood Red, Plate I, overlaid with velvet. Intermediate petal: outside surface—Carmine, Plate I, blotched with Pomegranate Purple, Plate XII; inside surface—Carmine and Ox-blood Red, Plate I, overlaid with velvet, except that it appears to be of a brighter hue. Inner petal: outside surface—same as intermediate except with white streak along center vein; inside surface—same as intermediate except with white streak along center vein.

This description was made from a rose that was open for three days, in a greenhouse, in the month of October, 1941, at Richmond, Indiana.

*Color.*—Outside petal: outside surface—Pansy Purple, Plate XII, penciled with Amaranth Purple, Plate XII; inside surface—base Amaranth Purple changing to Violet Carmine, Plate XII, to tip, overlaid with velvet covering. Inside petal: outside surface—Amaranth Purple, Plate XII, some with white streak along center vein; inside surface—Tyrian Rose, Plate XII, overlaid with Bordeaux, Plate XII, and all overlaid with a velvety covering.

*General color effect.*—Newly opened flower—Carmine, Plate I (Velvety). Three days open—Tyrian Rose, Plate XII, overlaid with Bordeaux, Plate XII, and all overlaid with a velvety covering.

*Behavior.*—Persist; fading purple.

*Flower longevity.*—On bush in garden, four days in September, 1941.

*Reproductive organs*

Stamens: Many; arranged regularly about pistils.

Filaments: Medium length; reddish; most with anthers.

Anthers: Medium size; reddish, brown; open at various times.

Pollen: Abundant; gold.

Pistils: Very many.

Styles: Uneven; medium long; medium heavy; bunched.

Stigma: White.

Ovaries: Some protruding from calyx.

Sepals: Permanent.

*Color.*—Inside—Light Cress Green, Plate XXXI, with fuzz covering. Outside—Cress Green, Plate XXXI.

*Plant*

Foliage:

*Leaves.*—Compound of 5 leaflets; very abundant; medium large; moderately heavy.

*Leaflets.*—Ovoid, with apex obtuse; base obtuse; margin simply serrate.

*Color.*—*Mature*: upper surface—Dark green; under surface—Light green. *Young*: upper surface—moderately bronze-red; under surface—very bronze-red.

*Rachis.*—Medium heavy. Upper side—grooved, hairy. Under side—moderately smooth, prickly.

*Stipules.*—Long; narrow; with moderately long points, turning out at an angle of less than 45°.

*Disease.*—Resistant to mildew, blackspot.

Growth:

*Habit.*—Bushy, upright; much branched.

*Growth.*—Vigorous.

*Canes.*—Medium heavy.

*Main stems.*—Bright green. *Thorns*—several; medium length; hooked downward; with short, narrow round base. *Prickles*—none. *Hairs*—none.

*Branches.*—Bright green. *Thorns*—several; medium length; hooked downward; with short, narrow round base. *Prickles*—none. *Hairs*—none.

*New shoots.*—Bright bronze-red. *Thorns*—several; medium length; hooked downward; with short round base. *Prickles*—none. *Hairs*—none.

I claim:

A new and distinct variety of Rose plant of the hybrid tea class, characterized as to novelty by its habits of growth, its improved foliage, and the color and size of its blossoms, substantially as shown and described.

ROY L. BYRUM.